United States Patent [19]
Zimmermann et al.

[11] Patent Number: 5,891,710
[45] Date of Patent: Apr. 6, 1999

[54] MICROORGANISMS FOR THE STABILIZATION OF PLASMIDS

[75] Inventors: Thomas Zimmermann, Naters; Cristiana Boraschi, Bioggio; Knut Burgdorf, Lalden, all of Switzerland; Cathérine Caubère, Nancy, France

[73] Assignee: Lonza Ltd., Gampel/Valais, Switzerland

[21] Appl. No.: 897,416

[22] Filed: Jul. 21, 1997

Related U.S. Application Data

[63] Continuation of Ser. No. 610,519, Mar. 4, 1996, abandoned, which is a continuation of Ser. No. 368,722, Jan. 4, 1995, abandoned, which is a continuation of Ser. No. 976,452, Nov. 13, 1992, abandoned.

[30] Foreign Application Priority Data

Nov. 21, 1991 [CH] Switzerland ............... 03 412/91-8

[51] Int. Cl.$^6$ ............................ C12N 15/74; C12N 15/52
[52] U.S. Cl. ............................. 435/252.3; 435/320.1; 435/106; 435/69.1; 536/23.2; 536/23.7
[58] Field of Search ................... 435/106, 252.3, 435/320.1, 69.1; 536/23.2, 23.7

[56] References Cited

U.S. PATENT DOCUMENTS

| 4,371,615 | 2/1983 | Miwa et al. ............... 435/115 |
| 4,650,761 | 3/1987 | Hershberger et al. ......... 435/172.3 |
| 4,920,048 | 4/1990 | Diderichsen ............... 435/69.1 |
| 5,198,343 | 3/1993 | DeGryse et al. ............ 435/69.1 |

FOREIGN PATENT DOCUMENTS

| 0178764 | of 1986 | European Pat. Off. . |
| 0477828 | 4/1992 | European Pat. Off. . |

OTHER PUBLICATIONS

Andresen et al., *J. General Microb.*, vol. 134, 1988, pp. 1737–1746.
Sakoda, H., et al., Journal of Fermentation and Bioengineering, vol. 69, No. 2, pp. 75–78, 1990.
Nagasawa, T., et al., Agricultural and Biological Chemistry, vol. 39, No. 7, pp. 1513–1514, Jul. 1975.
Landfald, B., et al., Journal of Bacteriology, vol. 165, No. 3, pp. 849–855, Mar., 1986.
Styrvold, O.B., et al., Journal of Bacteriology, vol. 165, No. 3, pp. 856 to 863, Mar., 1986.
Styrvold, O.B., et al., Journal of Bacteriology, vol. 165, No. 2, (1986), pp. 856–863.
Atkinson, K.D., et al., Journal of Bacteriology, vol. 141, No. 1, (1980), pp. 558 to 564.
White, R.F., et al., Journal of Bacteriology, vol. 113, No. 1, (1973), pp. 218 to 233.
Bioscience Reports, 5, (1985), pp. 29 to 37.
Gene, 39, (1985), pp. 173 to 180.
H. Sakoda and T. Imanaka, J. Ferment. and Bioeng., vol. 69, (1990), pp. 75 to 78.
Mol. Gen. Genet., 210, (1987), pp. 381 to 384.
J. Bacteriol., 171, (1989), pp. 4617 to 4622.
Gene, 26, (1983), pp. 273 to 282.
Gene, 36, (1985), pp. 27 to 36.
Plasmid, 8, (1982), pp. 45 to 54.
Kulla et al., Arch. Microbiol., 135, (1983), pp. 1 to 7.
J. Mol. Bil., 130, (1979), pp. 161 to 173.
Gene, 2, (1977), pp. 95 to 113.
Cohen et al., Proc. Natl. Acad. Sci., USA, 96, (1972), pp. 2110 to 2114.
Biotechnology, 1, (1983), pp. 784 to 791.
J. Bacteriol., 134, (1978), pp. 1141 to 1156.
Current Protocols In Molecular Biology, John Wiley and Sons, New York, (1989), section 3.16, Subcloning of DNA Fragments.
Lederburg and Cohen, J. Bacteriol., 119, (1974), pp. 1072 to 1074.
Harayama et al., J. Bacteriol., 167, (1986), pp. 455 to 461.
Current Protocols in Molecular Biology, John Wiley and Sons, New York, (1987), section 3.5.7 to 3.5.9.

*Primary Examiner*—Keith D. Hendricks
*Attorney, Agent, or Firm*—Fisher, Christen & Sabol

[57] ABSTRACT

New microorganisms with plasmids stable relative to betaine utilization. These new microorganisms contain (a) a hybrid plasmid with a DNA fragment that contains a genetic sequence that codes for betaine utilization and (b) a mutation in the chromosomal gene coding for the betaine utilization.

4 Claims, 1 Drawing Sheet

MICROORGANISMS FOR THE STABILIZATION OF PLASMIDS

This application is a Continuation of prior U.S. application Ser. No. 08/610,519, filed Mar. 4, 1996, now abandoned which is a Continuation of application Ser. No. 08/368,722, filed Jan. 4, 1995, now abandoned which is a Continuation of application Ser. No. 07/976,452, filed Nov. 13, 1992, now abandoned.

FIELD OF THE INVENTION

The invention relates to new microorganisms that are transformed with a new hybrid plasmid, which contains a new DNA fragment, and a process for their production as well as a process for the use of these microorganisms for a production strain with stable plasmids.

BACKGROUND ART

Generally it is known from molecularbiology that, for the production of specific compounds, microorganisms are transformed with a so-called "artificial" plasmid, in that the genes, which are coded for this specific compound, are introduced. A special problem of these plasmids is their instability, i.e., their property not to be transmitted in a controlled way to the daughter cells during the cell division of the microorganisms. The result is that more and more daughter cells occur during the fermentation process which contain no plasmid or fewer of the plasmid.

On a laboratory scale this plasmid loss can be countered by supplying the antibiotic to the culture medium whose corresponding gene which is resistant to antibiotics contains the plasmid. However, the addition of the appropriate antibiotic in fermentations on a large scale has proven to be disadvantageous. Thus, for example, some antibiotics, such as, tetracycline, show unfavorable effects on the ability of microorganisms which contain the plasmid to grow, divide and reproduce [*Bioscience Reports,* 5, (1985), pp. 29–37; *Gene,* 39, (1985), pp. 173–180]. Another drawback of antibiotic stabilization is that the addition of an antibiotic, especially in fermentation on a large scale, is too expensive. Further, the addition of an antibiotic in the production of pharmaceutical agents as well as in the production of food and feed additives is undesirable or unlawful.

Another method of how to counter this plasmid loss is described by H. Sakoda and T. Imanaka in J. Ferment. and Bioeng., Vol. 69, (1990), pp. 75–78. This method comprises a stable "recombinant host" plasmid system, in which first the tryptophan operon in the chromosome of the host is deleted and thus the host cell is inactive for the tryptophan transport. Then the host cell is transformed with a recombinant plasmid which carries this tryptophan operon. The selection of the host cells then takes place with this recombinant plasmid by means of the tryptophan transport. The drawbacks of this method are that, despite selection with tryptophan, in the actual fermentation process plasmid-free cells can also grow because of diffusion and thus daughter cells which contain no plasmid increasingly occur.

BROAD DESCRIPTION OF THE INVENTION

The main objective of the invention is to eliminate such drawbacks and to make available microorganisms having plasmids whose plasmids are structured so that they can be stabilized with an approved and easily available substance during the entire fermentation process and that the good ability of the microorganisms which contains the plasmid to grow, divide and reproduce has to be guaranteed. Other objectives and advantages of the invention are set out herein or are obvious herefrom to one skilled in the art.

The objectives and advantages of the invention are achieved by the microorganisms, hybrid plasmids, DNA fragments and processes of the invention.

The invention involves the betaine utilizing microorganisms which contains:

(a) a hybrid plasmid with a DNA fragment, containing a genetic sequence, that codes for the utilization of betaines and is characterized by the restriction map (I) below (see also FIG. 1):

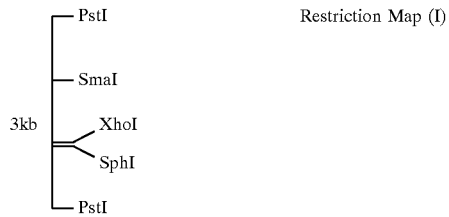

and (b) a mutation in the chromosomal gene, which codes for betaine utilization. Preferably microorganisms are those with the designation HK1349.4 which contain hybrid plasmid pL032 (DSM No. 6712).

The invention also involves the hybrid plasmid consisting of the above-identified DNA fragment and an expression vector. Preferably the hybrid plasmid is that with the designation pL032 consisting of the above-identified DNA fragment and the expression vector pKT240, as deposited in the microorganisms with the designation HK1349.4 (DSM No. 6712).

The invention also involves the above-identified DNA fragment, containing a genetic sequence, that codes for the utilization of betaines, and is characterized by the restriction map (I). Preferably the DNA fragment is that in hybrid plasmid pL032 as deposited in the microorganisms with the designation HK1349.4 (DSM No. 6712).

The invention further involves the process for the production of betaine utilizing microorganisms transformed with stable plasmids relative to betaine utilization, wherein:

(a) the chromosome of betaine utilizing microorganisms is mutated so that it is no longer capable of utilizing betaine;

(b) the isolated DNA fragment (identified above) that codes for betaine utilization is ligated in an expression vector to a hybrid plasmid; and (c) the microorganism obtained in step (a) is transformed with the hybrid plasmid obtained in step (b) and then selected relative to betaine utilization.

Preferably the process is that wherein:

(a) the chromosome of the betaine utilizing microorganism with designation HK1349 is mutated so that microorganisms HK1349.4 results;

(b) the isolated DNA fragment (identified above) that codes for betaine utilization is ligated in the expression vector pKT240; and (c) the microorganism with the designation HK1349.4 obtained in step (a) is transformed with hybrid plasmid pL032 obtained in step (b) and then selected relative to betaine utilization.

The invention also involves the DNA fragment (identified above) for the production of plasmids stable relative to betaine utilization.

The invention also involves using the invention betaine utilizing microorganisms for the production of production strains with plasmids stable relative to betaine utilization.

The invention also involves production strains with plasmids stable relative to betaine utilization obtainable by transformation of microorganisms containing a mutation in the chromosomal gene coding for the betaine utilization, with a hybrid plasmid (identified above) containing additionally a gene coding for a target-specific reaction. Preferably the production strains are those obtainable by transformation of microorganisms with the designation HK1349.4 with the preferred hybrid plasmid (identified above) containing additionally a gene coding for a specific reaction.

DETAILED DESCRIPTION OF THE INVENTION

Figure 1:
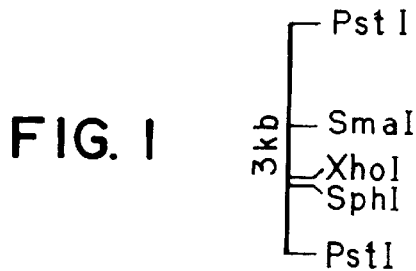
FIG. 1 is a restriction map (I) of the 3 kb PstI-cut DNA section.

The objective of the invention was able to be achieved with the microorganisms according to the invention, which are distinguished in that they contain (a) a hybrid plasmid with a DNA fragment, which contains a genetic sequence that codes for the utilization of betaines and is characterized by the restriction map (I) below (see also FIG. 1):

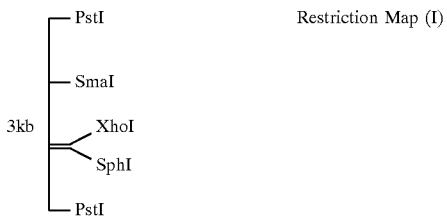

Restriction Map (I)

and (b) a mutation in the chromosomomal gene, coding for the betaine utilization. Examples of the betaine compounds are betaine, choline, dimethylglycine and sarcosine.

Production of microorganisms with stable plasmids

The production of the microorganisms according to the invention is explained in more detail below. The production takes place so that, in step (a):

I. Microorganisms which utilize betaine are mutated in the chromosome so that they are no longer able to utilize betaine, II. A DNA fragment which contains a genetic sequence that codes for the utilization of betaine is isolated, in step (b):

III. This isolated DNA fragment is introduced in an expression vector and by ligation, IV. A hybrid plasmid results. This hybrid plasmid, in step (c):

V. is introduced by transformation in the microorganism (host strain) obtained in step I and, after selection with betaine, microorganisms having plasmids stable relative to the betaine utilization are obtained.

VI. These transformed microorganisms represent a production strain having plasmids stable relative to betaine utilization, if their hybrid plasmid contains an additional gene coding for a specific reaction.

The production process is treated in more detail as follows:

I. Chromosomal mutation of betaine utilizing microorganisms

As microorganisms which utilize betaine, according to the invention all microorganisms can be used that grow with betaine or betaines as the sole (only) carbon, nitrogen and energy source. Examples of such microorganisms which utilize betaine are: Pseudomonas sp., Rhizobium/Agrobacterium sp. or Rhizobium sp..

Suitably the microorganisms of genus Rhizobium/Agrobacterium are used as the microorganisms which utilize betaine. Preferably microorganism Rhizobium/Agrobacterium sp. HK1349 (DSM No. 3944) is used. The Rhizobium/Agrobacterium sp. HK1349 was deposited on Nov. 4, 1991 in the Deutsche Sammlung fuer Mikroorganismen und Zellkulturen GmbH [German Collection for Microorganisms and Cell Cultures GmbH], Mascheroderweg 1b, D-3300 Brauschweig, with deposit number DSM No. 3944.

The mutation of the chromosomal gene coding for betaine utilization that is designed below as the beu, can take place according to methods which are conventional with one skilled in the art. Examples of such mutation methods are: deletion mutation by homologous recombination, frame shift mutation with a mutagenic agent and transposon insertion mutation.

Suitably the beu gene, in the case of Rhizobium/Agrobacterium sp. HK1349, is specifically removed or mutated from the microorganism chromosome by the method of homologous recombination. In this connection, first a DNA fragment which contains the beu gene is isolated from the microorganism chromosome and cloned in microorganisms with so-called "auxiliary" plasmids. Then from these "auxiliary" plasmids the desired DNA section coding for beu, whose isolation and identification are described below in (II), is deleted. Then with this so-called deleted "auxiliary" plasmid a corresponding deletion can be introduced chromosomally with methods which are conventional with one skilled in the art whereby the exchange is achieved by means of homologous recombination [*Mol. Gen. Genet.,* 210, (1987), pp. 381–384; *J. Bacteriol.,* 171, (1989), pp. 4617–4622].

Suitably the microorganisms Rhizobium/Agrobacterium sp. HK1349 (DSM 3944) are converted into the mutated beu-inactive (Beu$^-$) microorganisms HK1349.4 by the method of deletion mutation via homologous recombination.

II. Isolation of the DNA fragment beu

As the source of the DNA fragment beu, the microorganisms already described in (I) can be used. Preferably as the source for the DNA fragment beu the microorganisms Rhizobium/Agrobacterium sp. HK1349 with the DSM No. 3944, that are deposited as already described, are used.

For isolation suitably, first a DNA fragment, which contain a genetic sequence that codes for the utilization of betaines, is localized on the chromosome of Rhizobium/Agrobacterium sp. HK1349. The localization takes place with methods which are conventional with one skilled in the art, such as, by generation of a transposon insertion mutant in the corresponding microorganisms chromosome. In this way the desired DNA fragment beu is labeled with a transposon. The identification of the corresponding mutant with this labeled DNA fragment can then take place by not utilizing betaines as the carbon, nitrogen and energy source. Then the chromosomal DNA of the identified transposon insertion mutant is suitably deleted with the restriction enzyme EcoRI. The fragments obtained this way are cloned in *E. coli* by methods which are conventional with one skilled in the art via plasmids. The hybrid plasmids thus obtained and selected relative to transposon antibiotics resistance have a EcoRI-DNA fragment obtained from HK1349 and labeled with transposon with a size of 18.2 kb (12.5 kb and 5.7 kb for the corresponding transposon).

For the actual isolation of the intact (not labeled with transposon) DNA fragment beu, first the DNA from Rhizobium/Agrobacterium sp. HK1349 is isolated according to methods which are conventional with one skilled in the art. Then suitably the isolated DNA is completely digested with restriction enzyme EcoRI and separated. An EcoRI DNA fragment with a size of 12.0 to 13.0 kb is cloned in E. coli according to methods which are conventional with one skilled in the art. By "patch-mating" conjugation of the various clones with the beu-negative transposon labeled mutant, the clones that contain the intact gene beu can then be recognized and isolated by complementation of the mutation. The desired hybrid plasmid is then present in E. coli.

With the help of complementation tests with subclones (clones that exhibit deletions in various areas of the EcoRI DNA fragment) on the transposon mutant, a 3 kb PstI cut DNA fragment, containing a genetic sequence that is coded, identified and isolated for the use of betaines.

This DNA fragment is a component of the invention and is characterized by the restriction map (I) below:

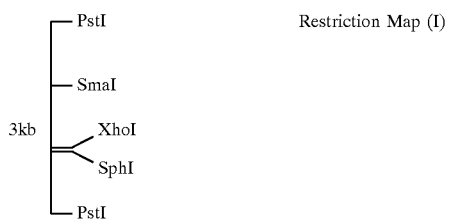

Restriction Map (I)

This DNA fragment is contained in hybrid plasmid pL032 and deposited in microorganism HK1349.4 (DSM No. 6712).

III. Ligation of the DNA fragment beu in expression vectors

The thus obtained DNA fragment beu can be ligated by the usual molecular biological techniques with an expression vector DNA which has previously been cleaved in the same way to give a hybrid plasmid.

Expression vectors usually contain a suitable promoter (expression control sequence). One or more singular cleavage sites for restriction enzymes are located behind this promoter, advantageously in the transcription direction. Then usually the desired gene section, in whose expression there is interest, is inserted into these cleavage sites.

For the hybrid plasmids according to the invention expression vectors with broad host range are used. Examples of such expression vectors are:

pKT240 [Gene, 26, (1983), pp. 273–282]
pME285 [Gene, 36, (1985), pp. 27–36]
pVK100 [Plasmid, 8, (1982), pp. 45–54].

Suitably for the hybrid plasmids according to the invention, expression vector pKT240 is cleaved with restriction enzymes PstI and the resultant restriction ends are ligated with DNA fragment beu by, e.g., T4 DNA ligase.

IV. Hybrid plasmids

The invention further relates to the thus resultant hybrid plasmids which contain the DNA fragment beu.

Basically all hybrid plasmids are suitable which replicate in the selected microorganism and can express the DNA fragment beu.

To achieve an effective expression in a hybrid plasmid, DNA fragment beu is placed in the transcription direction to the promoter. Especially suitable is hybrid plasmid pL032, which consists of DNA fragment beu and expression vector pKT240, in which DNA fragment beu is placed in the transcription direction to promoter $P_{bla}$ (which is responsible for the ampicillin resistance). This hybrid plasmid (in microorganism HK1349.4) was deposited on Sep. 17, 1991, in the Deutsche Sammlung fuer Mikroorganismen und Zellkulturen GmbH, Mascheroderweg 1b, D-3300 Braunschweig, with deposit number DSM No. 6712.

Figure 2:
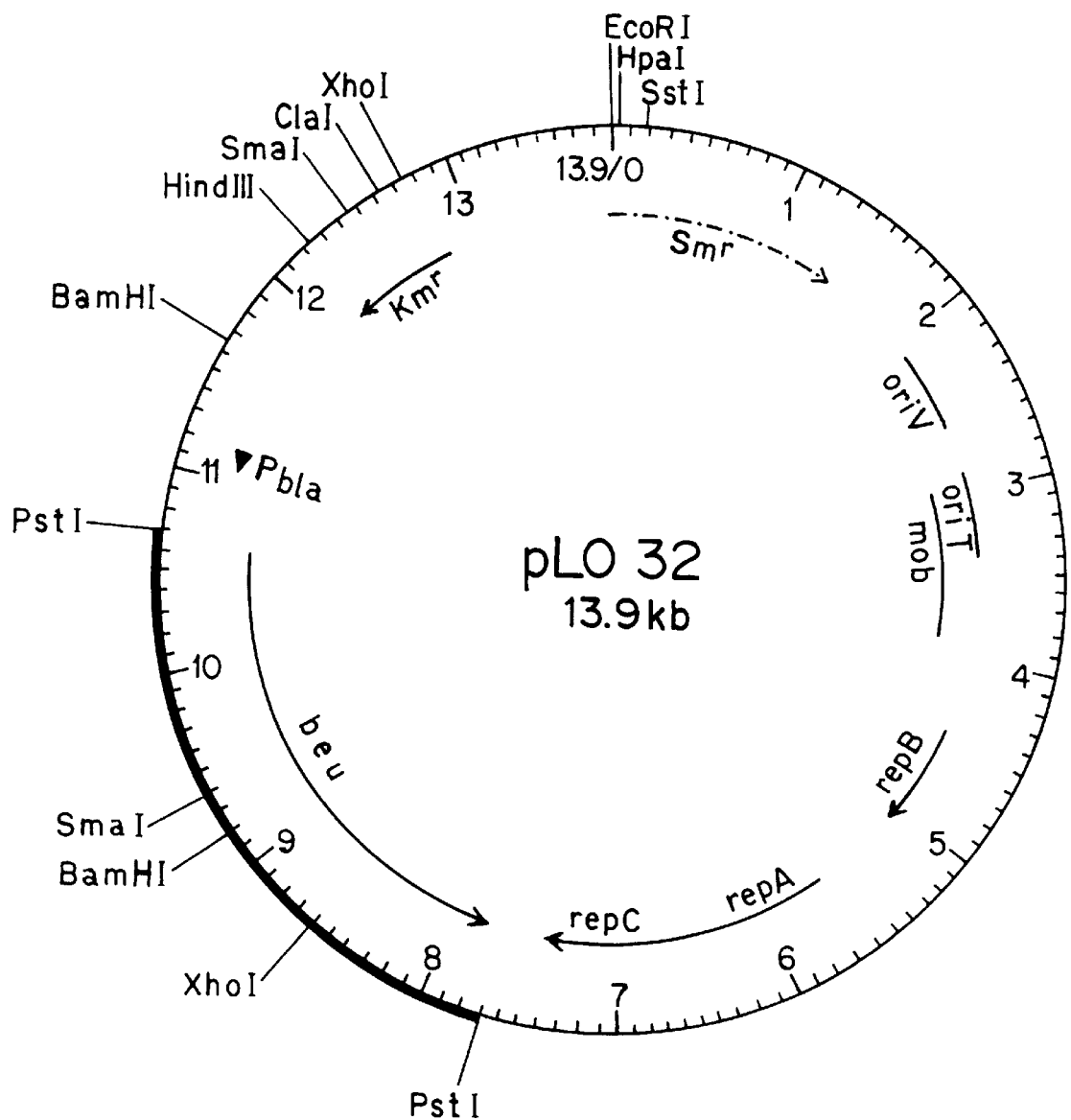
FIG. 2 is a diagram of hybrid plasmid pL032.

FIG. 2 shows a diagram of hybrid plasmid pL032.

V. Transformation

With the thus obtained hybrid plasmids the microorganisms obtained in step (I) are transformed. These transformed microorganisms are also a component of the invention.

The transformation of the microorganisms with hybrid plasmids according to the invention takes place according to known processes. The isolation or selection of the transformed microorganisms takes place on a selective nutrient medium to which betaine is added as the C or N source. If, as preferred, hybrid plasmid pL032 is used, the isolation or selection of the transformed microorganisms takes place on a nutrient medium to which betaine is added as the C or N source. Preferably, after transformation, microorganisms HK1349.4 are obtained with hybrid plasmid pL032 (DSM No. 6712). For stabilization of these transformed microorganisms suitably betaines in a concentration of 0.2 to 0.4 percent are added to the cultivation medium. As the cultivation medium those which are conventional with experts can be used, such as, a mineral salt medium according to Kulla et al., Arch. Microbiol., 135, (1983), pp. 1–7.

VI. Production strains with plasmids stable relative to betaine utilization

The invention relates both to the use of DNA fragment beu for the production of plasmids stable relative to the utilization of betaine and the use of microorganisms obtained with this stable plasmid after the transformation for the production of production strains with stable plasmids. Accordingly the resultant production strains are also a component of the invention. These production strains can be obtained by transformation of microorganisms which contains a mutation in the chromosomal gene coding for betaine utilization, with a hybrid plasmid of the gene coding for a target-specific conversion additionally to DNA fragment beu.

These stable plasmids, containing beu and the additional gene, can be obtained by methods which are conventional with one skilled in the art, either:

e.g., by ligation of the additional gene in a hybrid plasmid which contains beu, or e.g., by ligation of the DNA fragment beu in a hybrid plasmid, that already contains a gene coded for a target-specific use.

Suitably if a hybrid plasmid is used that already contains the additional gene, the latter is cut (linearized) with restriction enzyme PstI and then ligated with the PstI DNA fragment beu to the stable plasmid.

If the hybrid plasmid which will be used already contains DNA fragment beu, the linearization suitably takes place with the restriction enzymes that "flank" the additional gene. The vector correspondingly cut with beu and the additional DNA fragment are religated.

After renewed transformation in the microorganisms according to the invention, the latter can guarantee the desired reaction without plasmid loss during the cultivation with betaines.

Preferably hybrid plasmid pL032 is used as the stable plasmid, which contains an additional gene coding for a target-specific conversion. This stable plasmid basically corresponds to hybrid plasmid pLO32. Preferably then this stable plasmid is transformed into microorganism HK1349.9.

Plasmid pLOL01 as a stable plasmid which contains microorganism HK1349.4 is used as an example for a production strain with stable plasmids. For the production of pLOL01 the hybrid plasmid pLO3 already described in European Published Patent Application No. 0477828, which consists of expression vector pKT240 and the gene xylMA (coding for the enzyme xylene-monooxygenase), is linearized with restriction enzyme PstI and then ligated with DNA fragment beu. PLOLO1 basically corresponds to hybrid plasmid pLO32. In contrast to pLO32, pLOLO1 additionally contains the xylMA genes.

After transformation of pLOL01 in microorganism HK1349.4 this production strain is able to convert 2,5-dimethylpyrazine into 5-hydroxymethylpyrazine in the presence of betaine without plasmid loss.

EXAMPLE 1

Generation of a transposon (Tn5) insertion mutant and its phenotypic identification The strain Agrobacterium/Rhizobium sp. HK1349 (DSM 3944) was brought to the development of a spontaneous resistance relative to streptomycin (1000 μg/ml) by selection pressure. This resistance was demonstrably stable without selection over 50 generations and was used as selection marker. 0.2 ml of a Tn5-donor culture, E. coli S17-1/pSUP 2021 [neomycin resistant; R. Simon et al., Biotechnology, 1, (1983), pp. 784–790], was mixed with 2 ml of recipient culture HK1349 and centrifuged. The cells were washed in 0.9 percent saline (NaCl solution) and resuspended in 100 μl of 0.9 percent saline. The conjugation of the recipient strain with the donor strain took place overnight at 30° C. on dry nutrient agar. Then the cells were harvested and plated out in dilutions on a selection medium below for recipient and transposon. Tn5-mutants of HK1349 were obtained by selection from nutrient agar with streptomycin (1000 μg/ml) and neomycin (100 μg/ml). Phenotypic identification was achieved by nonuse of betaines as the C or N source in mineral salt medium [Kulla et al., Arch. Microbiol., 135, (1983), pp. 1–7].

EXAMPLE 2

Cloning of the Tn5-labeled DNA fragment from HK1349 genome

According to a known method isolated chromosomal DNA [J. Mol. Biol., 130, (1979), pp. 161–173] of Tn5-mutated HK1349 (5 μg) was completely digested with EcoRI (4 units/μg). 2.5 μg of plasmid pBR325 [Gene, 2, (1977), pp. 95–113] was treated (dephosphorylized) after complete digestion by EcoRI (1 unit/μg) with alkaline phosphatase (0.1 unit/1–20 pmol DNA termini). Recombinant hybrid plasmids were obtained by the mixing of genomic DNA and pBR325 with T4-DNA ligase [0.2 units/μg DNA) in 400 μl of ligation buffer [20 mM of Tris-HCl, pH 7.2, 10 mM of dithioerythritol (DDT), 10 mM Of MgCl$_2$, and 0.6 mM of adenosinetriphospate (ATP)]. The mixture was incubated overnight at 12° C. Aliquots of the ligation mixture were used in the transformation experiment according to Cohen et al. [Proc. Natl. Acad. Sci., USA, 96, (1972), pp. 2110–2114] with E. coli ED8654. The transformants were selected for their resistance to ampicillin (100 μg/ml, pBR325) and kanamycin (25 μg/ml Tn5-labeled insert) on nutrient agar. All cloned hybrid plasmids had a HK1349 insert (12.5 kb+5.7 kb for Tn5), which was labeled with Tn5. An accurate restriction mapping documented the transposon insertion in the same genomic fragment at the same point which corresponds to identical phenotype Beu⁻(inactive beu gene by Tn5-insertion; genotype beu) of the selected Tn5-mutants. These mutants are designated as HK4V11 below.

EXAMPLE 3

Cloning of the DNA fragment beu (unlabeled) from the HK1349 genome

HK1349 DNA was isolated corresponding to Example 2, completely digested with EcoRI (4 units/μg) and separated by agarose gel electrophoresis. The DNA fragments were isolated in a range of 12.0 kb to 13.0 kb (labeled fragment had the size 12.5 kb) from agarose electrophoresis gels. The isolated DNA was cut corresponding to Example 2 with EcoRI and ligated with the dephosphorylized vector pVK100 [Plasmid, 8, (1982), pp. 45–54] corresponding to Example 2. Aliquots of the ligation mixture were used in the transformation experiment in E. coli S17-1 [Biotechnology, 1, (1983), pp. 784–791] corresponding to Example 2. The transformants were selected for their resistance to tetracycline (25 μg/ml) and kanamycin (25 μg/ml) from nutrient agar. The obtained transformants were examined by "patch mating" conjugation with transposon mutant HK4V11 (beu) as the recipient strain for insertion of the desired DNA section with gene beu: antibiotic resistant transformants were inoculated in a fixed pattern for selection medium (nutrient agar with kanamycin 2 μg/ml). Nutrient agar plates were inoculated parallel with a lawn of recipient strain HK4V11. For the conjugation the transformants were labeled as individual clones on the grown cell lawn of the recipient strain and incubated overnight at 30° C. The "mating" plates were finally labeled for selection of the obtained transconjugants on the mineral salt medium with betaine (0.2 percent by weight) cited in Example 1, as substrate, which donor and recipient cannot utilize. With the increasing transconjugant the mutated genomic DNA section of recipient (HK4V11) was complemented (or homologously recombined) by the intake of a hybrid plasmid with the corresponding intact DNA area from the donor strain. Complementing hybrid plasmids received the designation pVK100s. For suppression of revertants of strain HK4V11, neomycin (100 μg/ml) was added to the medium. By hybridization against the cloned, Tn5-labeled DNA fragments, the successful cloning of the complementing fragment with the intact beu gene from HK1349 genome on the hybrid plasmid pVK100s was able to be confirmed.

EXAMPLE 4

Identification of DNA subfragments coded for beu

By deletion clonings with various restriction enzymes (BglII, XhoI, SphI, PstI) on hybrid plasmid pVK100s and then complementations to beu Tn5-mutant HK4V11, a 3 kb PstI-cut DNA section was able to be identified on the plasmid, which codes for the betaine utilization. This section is characterized by the following restriction map (I):

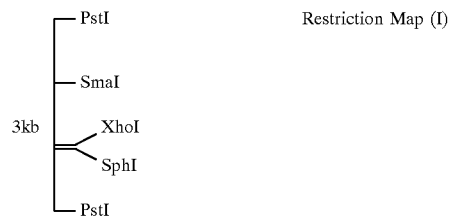

Restriction Map (I)

See also FIG. 1, which also sets out restriction map (I).

EXAMPLE 5
Stable mutation of beu in HK1349 genome

Basically, since a Tn insertion mutation with and without antibiotic selection is very unstable, a stable deletion mutation was introduced to strain HK1349. In this case a convention method of homologous recombination was the procedure used: The 12.5 kb EcoRI fragment obtained in Example 3 was cloned in the suicide vector pACYC184 [*J. Bacteriol.*, 134, (1978), pp. 1141–1156] not expressed in HK strains and from that the 3 kb PstI fragment coding the beu was deleted by restriction with PstI (1 unit/µg). The religation took place overnight with 1 unit/µg of T4-DNA ligase. The deletion hybrid pCC6 was transformed in *E. coli* HB101/pRK2013 (helper plasmid for mobilizing pCC6) and was able to be infiltrated from that by conjugative transfer in HK1349. The obtained transconjugants were selected against the auxotrophy of the donor (Pro−; proline negative) and for antibiotic resistance of the plasmid [mineral salt medium 0.4 percent glucose and tetracycline (25 µg/ml)]. Only cells which integrated the plasmid chromosomally by homologous recombination have tetracycline resistance and can grow on the medium. To again remove vector pACYC184 and the intact beu gene from the HK1349 chromosome by a second recombination event, these transconjugants were cultivated over 100 generations in the same medium without selection by tetracycline. Then to increase the number of tetracycline sensitive beu mutants, a selection was performed against the integrated vector pACYC184 and the intact beu gene. For this purpose the cells were taken up in 25 ml of complex medium NYB (Oxoid, Wesel, F.R.G.) tetracycline (10 µg/ml) and incubated for 6 hours at 30° C. Then to kill the growing (tetracycline resistant) cells 0.5 mg/ml of D-cycloserine and 15 mg/ml of penicillin G were added to the culture. After another incubation at 30° C. for 84 hours, the cells were centrifuged, washed three times in fresh NYB and platted in a suitable dilution on nutrient agar. 18 percent of the obtained colonies were tetracycline sensitive, and a third thereof was at the same time also negative in the utilization of betaine. The correct introduction of the deletion of beu was confirmed by hybridization against the 12.5 kb fragment in hybrid plasmid pVK100s (from Example 3). (Only an EcoRI fragment shortened by 3 kb was labeled.) The resultant mutant HK1349.4 was able to be complemented by the 3 kb PstI fragment (beu) cloned in suitable vectors. The vectors are described below in Example 6.

EXAMPLE 6
(a) Cloning of the beu gene in diverse "broad host range vectors"

The 3 kb PstI fragment which codes for beu was cloned in the known "broad host range expression vectors" pKT240, pME285 and pVK100 [*Current Protocols in Molecular Biology*, John Wiley and Sons, New York, (1989), section 3.16, Subcloning Of DNA Fragments]. In this case the correct orientation of the insert to the promoter played a role. In the case of pKT240, the correct orientation of the insert (arrangement in transcription direction) to promoter $P_{bla}$ (promoter of gene bla, which is responsible for the ampicillin resistance) played a role here.

(b) Insertion of beu in pKT240 pKT240 was "linearized" with PstI (1 unit/µg). This "linearized" DNA was ligated with the 3 kb PstI fragment (insert) with T4-DNA ligase (1 unit/µg) in the ligation buffer (20 mM of Tris-HCl, pH 7.2, 10 mM of DTT, 10 mM of $MgCl_2$, and 0.6 mM of ATP). The ligation took place overnight at a temperature of 12° C. First, the obtained ligation mixture was conjugated according to the method of Lederberg and Cohen [*J. Bacteriol*, 119, (1974), pp. 1072–1074] in *E. coli* S.17-1. The selection took place on NYB with kanamycin, 25 µg/ml, and against ampicillin, 100 µg/ml. Hybrid plasmids with the insert (ampicillin sensitive, kanamycin resistant) in transcription direction for promoter $P_{bla}$ received the designation pL032.

(c) Conjugation of pL032 in HK1349

The conjugative transfer of pL032 from *E. coli* S17-1 in HK1349.4 also took place according to the above described method. The selection of HK1349.4 which contains hybrid plasmid pL032 took place directly on the betaine utilization to be complemented (mineral salt medium as in Example 1 containing 0.2 percent by weight of betaine).

EXAMPLE 7
Stabilitiy of pL032 in HK1349.4

The long time stability of the hybrid plasmid in microorganism HK1349.4 was tested on different media. Clearly the stabilization took place by the utilization of the sole (only) C source, betaine, as the substrate (or other betaines, such as, choline and dimethylglycine) to 100 percent. In limiting nitrogen, as in a N-free medium in a continuous recycling culture, stabilization has been proven up to the 100 percent level when using betaine as the sole (only) N source in the presence of other C sources. The tests are set out in following Table I.

TABLE I

| MEDIUM | TOTAL CELLS | CELLS WITH PLASMID |
|---|---|---|
| MM (with ammonium sulfate) 0.2% Glc (A + N) (no selection) | 100% | 5% |
| MM (without ammonium sulfate) 0.1% Bet (A − N) 0.1% Glu (no selection) | 100% | 20% |
| MM (without ammonium sulfate) 0.2% Bet (A − N) (C and N source) | 100% | 100% |
| MM (with ammonium sulfate) 0.2% Bet (A + N) (C source) | 100% | 100% |
| MM (without ammonium sulfate) 0.1% Bet (A − N) (N source) 0.2% Glc | 100% | 100% |

Abbreviations in the table:
Glu = L-glutamate (C & N source)
Glc = glucose (C source)
N = nitrogen +, −
Bet = betaines (C & N source)
MM = minimal medium [Kulla et al., Arch. Microbiol., (1983), 135, pp. 1–7]

EXAMPLE 8
Stability of a hybrid plasmid with biotransformation properties

As an example for the stabilizing effect of plasmid coded beu gene in the beu negative host strain HK1349.4, hybrid plasmid pL03 was selected, which was previously described in European Published Patent Application No. 0477828. This is a hybrid plasmid consisting of vector pKT240 and a ClaI-HindIII fragment (2.35 kb) of the TOL-plasmid which codes for the gene xylMA and was cloned under the control of the kanamycin phosphotransferase promoter.

(a) Introduction of a new kanamycin resistance ($Km^R$)

The kanamycin resistance casette (1.1 kb) from pRME1 [Harayama et al., J. Bacteriol., 167, (1986), pp. 455–461] was cut out with EcoRI (4 U per µg DNA) and isolated by agarose gel electrophoresis. 5'-projecting ends of the DNA fragment were filled up by the Klenow-Raktion method [Current Protocols In Molecular Biology, John Wiley, New York, (1987), section 3.5.7to 3.5.9]. The pL03 DNA was cut with HpaI (1 U per μg DNA) and dephosphorylized with 4.8 U of alkaline phosphatase. After isopropanol precipitation this "blunt end" cut vector with the now "blunt end" insert ($Km^R$ casette) was ligated overnight at 15° C. Ligation buffer: 20 mM of Tris, 10 mM of $MgCl_2$, 0.6 mM of ATP, pH 7.2, 10 percent of PEG 6000, and 0.5 U of T4 DNA ligase.

E. coli K12 was transformed with the ligation mixture in an analogous way to Example 2 and transformants containing pL03 ($Km^R$) were selected on nutrient agar with 50 μg/ml Km.

(b) Introduction of beu-gene in pL03 ($Km^R$)

The hybrid plasmid pL03 ($Km^R$) was "linearized" (cf. Example 6) with PstI (1 U/μg DNA) and ligated with the 3 kb PstI fragment beu. Transformation in E. coli and conjugation in HK1349.4 took place corresponding to Example 6. The hybrid plasmid received the designation pLOLO1 and corresponds to pL032 with additional xylenemonooxygenase-activity (xylMA).

(c) Biotransformation with stabilized hybrid plasmid

Agrobacterium/Rhizobium sp. HK1349.4/pLOL01 was cultivated in mineral salt medium [Arch. Microbiol., 135, (1983), pp. 1–7] with 0.2 percent betaine as the sole (only) carbon source at 30° C. The biotransformation of 0.1 percent (v/v) 2.5-dimethylpyrazine in 5-hydroxymethyl-2-methylpyrazine was proven. The yield of 5-hydroxymethyl-2-methylpyrazine was 20 percent after 2 days.

d) Stability of pLOLO1 in HK1349.4

Analogous to Example 7, the long-time stability of the hybrid plasmid in microorganism HK1349.4 was tested. Both by the use of betaine as the sole (only) C source and as a sole N source, the plasmid was also able to remain stable in the producer strain under biotransformation conditions up to 100 percent.

What is claimed is:

1. A microorganism of the genus Agrobacterium/Rhizobium having the designation HK1349.4 which is able to grow on media which contains betaines as the sole C- and/or N-source, containing:

(a) hybrid plasmid pL032 (DSM No.6712) having a DNA fragment, which contains a genetic sequence, which codes for a protein which confers the ability to grow on media which contains betaines as the sole C- and/or N-source, and which is characterized by the following restriction map (I):

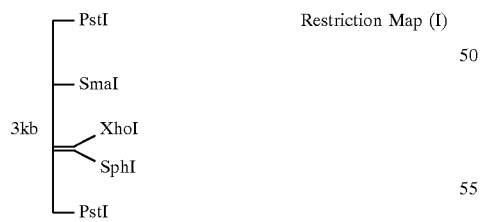

; and (b) a mutation of a chromosomal gene required for growth on media which contains betaines as the sole C- and/or N-source, the mutation eliminating ability for growth on said media.

2. A hybrid plasmid having the designation pL032 (DSM No. 6712) consisting of:

(a) a DNA fragment, which contains a genetic sequence, which codes for a protein which confers the ability to grow on media which contains betaines as the sole C- and/or N-source, and which is characterized by the following restriction map (I):

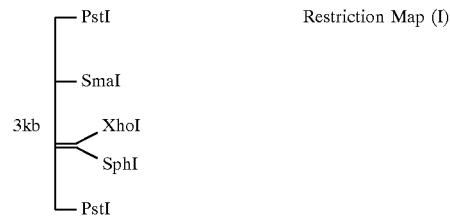

; and (b) an expression vector pKT240 as deposited in a microorganism having the designation HK1349.4 (DSM No. 6712).

3. A process for the production of a microorganism from the genus Rhizobium/Agrobacterium having the designation HK1349.4 containing plasmid pL032 (DSM No. 6712) which confers the ability to grow on media which contains betaines as the sole C-and/or N-source, comprising:

(a) mutating a chromosomal gene of the microorganism having the designation HK1349 so that the microorganism HK1349.4, a microorganism deficient in the ability to grow on media which contains betaine as the sole C- and/or N-source, results;

(b) isolating a DNA fragment from an organism of the genus Rhizobium/Agrobacterium, which contains a genetic sequence, which codes for a protein which confers the ability to grow on media which contains betaine as the sole C- and/or N-source, and which is characterized by the following restriction map (I):

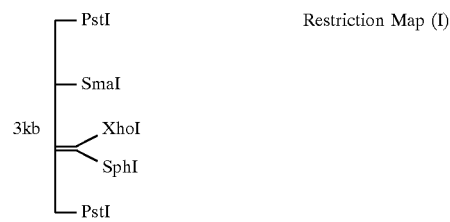

(c) ligating the DNA fragment from step (b) in expression vector pK240 so that plasmid pL032 results; and (d) transforming the microorganism having HK1349.4 obtained in step (a) with the hybrid plasmid pL032 obtained in step (c) and, then, selecting for bacteria with the ability to grow on media which contains betaines as the sole C- and/or N-source.

4. A production strain obtained by transformation of a microorganism having the designation HK1349.4 containing a mutation of a chromosomal gene required for growth on media which contains betaine as the sole C- and/or N-source with a hybrid plasmid having the designation pL032 consisting of a DNA fragment, which contains a genetic sequence, which codes for a protein which confers the ability to grow on media which contains betaines as the sole C- and/or N-source, and which is characterized by the following restriction map (I):

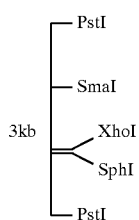
Restriction Map (I)
and of an expression vector pK240, as deposited in the microorganism having the designation HK1349.4 (DSM No. 6712), the hybrid plasmid additionally containing a xylene-monooxygenase gene, the activity of which is measured by the conversion of 2,5-dimethylpyrazine into 5-hydroxymethylpyrazine.
* * * * *